United States Patent [19]

Alrazi

[11] 4,124,025
[45] Nov. 7, 1978

[54] GAS LOCK FOR HYPODERMIC

[76] Inventor: Jamil A. R. Alrazi, 108 Mills St., Morristown, N.J. 07963

[21] Appl. No.: 775,798

[22] Filed: Mar. 9, 1977

[51] Int. Cl.² .............................................. A61M 5/00
[52] U.S. Cl. ................................ 128/218 R; 128/221; 128/2 F
[58] Field of Search ............. 128/2 F, DIG. 5, 218 R, 128/218 N, 220, 221, 215, 276, 261, 235

[56] References Cited

U.S. PATENT DOCUMENTS

| | | | |
|---|---|---|---|
| 2,400,722 | 5/1946 | Swan | 128/215 X |
| 2,862,496 | 12/1958 | Hassler et al. | 128/261 |
| 2,940,448 | 6/1960 | Furlong, Jr. | 128/DIG. 5 |
| 3,162,195 | 12/1964 | Dick | 128/DIG. 5 |
| 3,882,866 | 5/1975 | Zackheim | 128/235 |

Primary Examiner—John D. Yasko
Attorney, Agent, or Firm—Darby & Darby

[57] ABSTRACT

A gas lock for a hypodermic unit used to collect blood for blood gas analysis is disclosed. The gas lock comprises a cylindrical container adapted to receive the puncturing end of the hypodermic needle and a semi-solid substance, such as a mixture of petroleum jelly and paraffin, is located within the container and positioned so as to be penetrated by, and to envelop, the puncturing end of the needle. Gases in the blood are thereby prevented from escaping from the hypodermic unit and ambient gases are prevented from entering the unit and contaminating the blood gases. The gas lock further includes a rubber gripping band positioned in the upper portion of the container so as to be aligned with the end of the hypodermic needle adjacent to the syringe. The gripping band facilitates the disconnection of the needle from the syringe so that the syringe, containing the withdrawn blood which is to be analyzed, may be connected to testing apparatus.

11 Claims, 4 Drawing Figures

U.S. Patent　　　　Nov. 7, 1978　　　　4,124,025
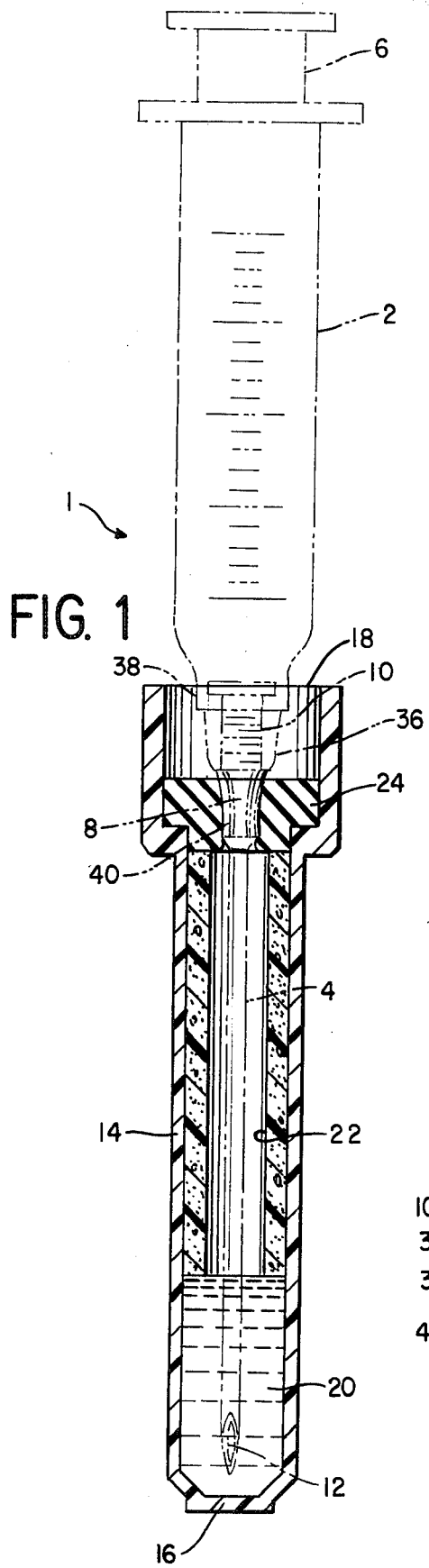
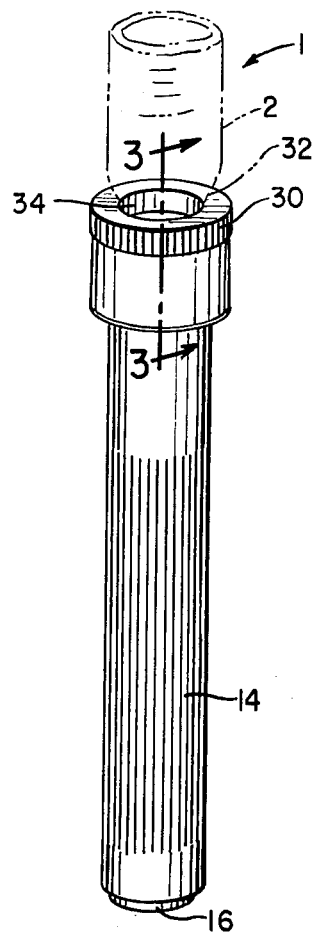
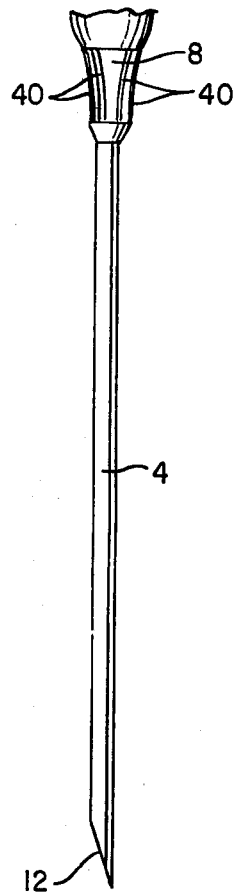
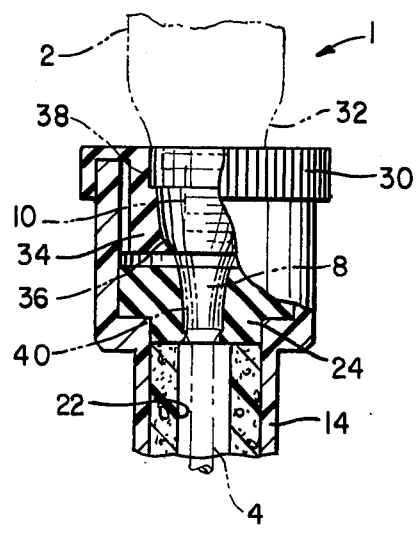

GAS LOCK FOR HYPODERMIC

This abstract is not to be taken either as a complete exposition or as a limitation of the present invention, however, the full nature and extent of the invention being discernible only by reference to and from the entire disclosure.

BACKGROUND OF THE INVENTION

This invention relates to a gas lock for hypodermic needles and more particularly to such a needle used in conjunction with a hypodermic syringe containing blood which is to be analyzed with regard to the gases dissolved therein.

As is well known in the field of medicine, it is frequently valuable, in diagnosing a patient's illness, to analyze the gases dissolved in the patient's blood and the equipment for analyzing such gases is universally available. A problem arises, however, in that the accuracy of the analysis is determined by an ability to analyze the blood as withdrawn from the patient with a minimal amount of the blood gases evolving from the solution and being lost, and with a minimum amount of contamination of the blood by the dissolution therein of gases from the surrounding atmosphere after the blood has been withdrawn. In this regard it is noted that, as a practical matter, a substantial period of time frequently elapses between the time the blood is withdrawn from the patient and the time it reaches a laboratory for analysis.

Medical personnel, recognizing the loss of accuracy caused both by contamination of the blood and by its "staleness", that is, gases originally dissolved in the blood have evolved out, have devised various means to minimize the lack of accuracy. For example, it has been proposed that the hypodermic syringe be inserted into a rubber stopper immediately after blood withdrawal, thereby sealing the single gas passage in the hypodermic unit (syringe and needle). In this regard, medical technicians frequently take the extraordinary measure of destroying expensive evacuated containers, commonly known as "vacutainers", merely to obtain the rubber stoppers from such containers. Theoretically, this should provide a satisfactory solution to the aforementioned problem. As a practical matter, however, it has not been satisfactory. This is due to the fact that the rubber stoppers frequently become dislodged from the hypodermic needles thereby permitting blood gas loss and permitting contamination of the blood. Further, the hypodermic needles are frequently drive completely through the rubber stoppers resulting in the open, puncturing, end of the needle not being within, and enveloped by, the rubber stopper. This last defect, of course, causes an additional problem in that the sharply pointed puncturing end of the hypodermic needle is exposed and can therefore injure medical personnel handling the hypodermic units. Finally, utilization of a rubber stopper only at the puncturing end of a hypodermic needle suffers from the additional defect that the slender hollow needle may easily be broken, thereby both permitting contamination or gas leakage and resulting in a sharply pointed instrument being exposed.

SUMMARY OF THE INVENTION

It is, therefore, an object of the present invention to provide a gas lock for a hollow needle whereby the aforesaid drawbacks and disadvantages may be most efficaciously avoided.

It is another object of the invention to provide such a gas lock which will both prevent ambient gases from entering the needle and prevent blood gases from escaping through the needle.

It is still another object of the instant invention to provide such a gas lock which will minimize the breakage of the needles.

It is a further object of the invention to provide such a gas lock which will be relatively inexpensive.

It is yet another object of the invention to provide such a gas lock which will enable the easy disconnection of the needle from a syringe to which it is attached.

Generally speaking, the objectives of the present invention are attained by the provision of a gas lock for a hollow needle having a puncturing end comprising a container adapted to receive the puncturing end of the needle, and a semi-solid substance located within the container and positioned to be penetrated by, and to envelop, the puncturing end of the needle, whereby gas is prevented from escaping from, or entering into, the puncturing end of the needle.

The objectives of the invention are also attained by the provision of the combination of a hypodermic unit, including a needle and syringe, and a gas lock for the unit, the gas lock comprising a container adapted to receive the puncturing end of the needle, and a semi-solid substance located within the container and positioned to be penetrated by, and to envelop, the puncturing end of the needle, whereby gas is prevented from escaping from, or entering into, the puncturing end of the needle.

BRIEF DESCRIPTION OF THE DRAWINGS

The foregoing and other objects and features of the present invention will be more clearly understood from the following detailed description thereof when read in conjunction with the accompanying drawings, in which:

FIG. 1 is a longitudinal sectional view of the gas lock of the instant invention with a hypodermic syringe and needle illustrated in phantom lines;

FIG. 2 is a perspective view of the inventive gas lock including a cap portion;

FIG. 3 is a plan view, partly in section, taken along lines 3—3 of FIG. 2; and

FIG. 4 is a plan view of a prior art hypodermic needle particularly adapted for use with a gas lock of the instant invention.

DESCRIPTION OF THE PREFERRED EMBODIMENTS

Turning now to FIG. 1, there is illustrated a hypodermic unit 1 including a syringe 2 and a needle 4, the entire unit being illustrated in phantom lines. As is well known in the medical art, a conventional hypodermic unit such as the one illustrated is used to withdraw blood from patients so that the blood may subsequently be analyzed. In particular, the apparatus illustrated is utilized when it is desired to analyze the gases dissolved in the patient's blood. The syringe portion 2 is usually made from plastic or glass and includes a plunger or piston rod 6 and a piston (not shown). The hypodermic needle portion 4 of the hypodermic unit is a hollow, elongated tubular structure, the major portion of which is conventionally made of metal and the upper portion of which, indicated at 8, may be of either metal or plastic. The lower portion of the needle 4 is bevelled to facilitate piercing or puncturing the skin of a patient while the upper end of the needle is configured so as to facilitate its attachment to the syringe portion of the hypodermic unit. Generally, hypodermic units utilized for drawing blood are constructed so that the lower portion of the syringe, indicated at 10, is internally threaded and the upper portion of the needle 8 is externally threaded, the two ends mating in what is known in the art as a Luer-Loc, such a closure being airtight.

Although the needle-syringe connection is, as just indicated, airtight, it will also be clear that gases can freely enter and leave the combination through the aperture, indicated at 12, in the lowermost part of the needle 4. Usually, this poses no problem. However, when the blood which has been withdrawn is subsequently to be analyzed for its gas content, it is clear that some steps must be taken to prevent the blood gases which are dissolved in the blood contained within the syringe 2 from being transmitted out of the hypodermic unit through the aperture or orifice 12. Further, to avoid contamination, it is necessary that the ambient air be prevented from entering, via aperture 12, the syringe, where the air will dissolve in the blood there contained thereby causing erroneous test results. To this end there is provided a tubular container 14, which may be made of glass, plastic or metal. The container 14 is closed at its lower end 16 and is open at its upper end 18. The container 14 is configured to receive the puncturing end of the hypodermic needle 4. The upper end 18 of the container may have the same diameter as the median portion thereof, or it may be of a larger diameter, as illustrated in FIG. 1, which illustrated structure is suitable for use with a cap as will be discussed below with regard to FIGS. 2 and 3.

Located within the container 14 is a semi-solid substance 20 which may, for example, be a mixture of paraffin, such as that sold under the brand name "Tissuemat" by the Fisher Scientific Company, and petroleum jelly, such as that sold under the brand name "Vaseline" by Chesebrough-Pond's Inc. The semi-solid substance may also be, for example, a caulking compound such as that sold under the name "Dap 33" by Dap Inc. Although numerous semi-solid substances will be useful for the purpose herein, it has been found that the first-mentioned mixture, that is paraffin combined with petroleum jelly, makes a particularly satisfactory substance. Specifically, a mixture of 80 ccs of melted paraffin mixed with 20 ccs of petroleum jelly has been found to provide a suitable mixture. The function of the semi-solid substance is to surround and envelop the aperture 12 of the needle 4 and its purpose is twofold. Firstly, its purpose is to prevent ambient gases from entering the blood maintained within the syringe 2 where such ambient gases might be dissolved, thereby contaminating the sample to be tested and causing erroneous test results. Secondly, the purpose of the substance is to prevent the gases which have evolved out of solution in the blood from escaping through the aperture 12. To serve its purposes, the semi-solid substance 20 must be located within the container in such a position as to be penetrated by the puncturing end of the needle 4 and it must further be located so that when the needle 4 is inserted into the container 14, the substance 20 will envelop aperture 12. It will therefore be realized that where the container length is only slightly greater than the length of the needle, as illustrated in FIG. 1, the semi-solid substance 20 must be at least in the lower portion of the container 14 and, as illustrated, the substance is used to fill approximately the lower quarter of the container. It will further be clear, however, that in the event that a container substantially longer than the needle is utilized, then, as previously noted, it is necessary that the substance 20 be so located that when the needle 4 is inserted into the container, the puncturing end will pierce, and the aperture 12 will be enveloped by the substance 20. Further, a major portion of the container 14 may be filled with the substance 20. The only limitation on the quantity of the semi-solid substance utilized is that the substance should not be permitted to rise to the level of the bottom of the syringe 2 when the needle 4 is inserted into the container 14. This is to insure that none of the substance 20 can enter into the syringe 2 where it can mix with, and contaminate, the blood.

In the embodiment illustrated in FIG. 1, the upper three quarters of the container 14 is filled with a porous solid material 22, such as styrofoam. The material 22 is porous so that the needle 4 can be easily inserted to a depth such that the puncturing end penetrates the substance 20, and the material 22 is a solid, rather than a liquid, so that it will prevent the leakage of the substance 20 from the container in the event that the container is stored in an inverted position. It will be realized, of course, that if a non-flowing substance such as rubber is utilized as the semi-solid substance 20, then it is unnecessary to use a material 22 and the space between the upper portion of the substance 20 and the upper end 18 of the container 14 may be unfilled.

Positioned within the upper portion of the container 14 is a rubber gripping band 24. The purpose of this gripping band is two-fold. Firstly, band 24 serves to snugly grip the upper portion 8 of the needle 4 thereby serving to retain the hypodermic unit within the container 14 subsequent to the insertion of the unit into the container. Secondly, the gripping means 24 serves to grip the vertical ribs (illustrated in FIG. 4) which are conventionally formed in the upper portion 8 of the needle 4. The gripping action provided by the gripping means 24 serves to facilitate the rotation and removal of the needle 4 (still frictionally adhered to the container 14) from the syringe 2, the syringe 2 being the portion of the hypodermic unit which is inserted into conventional apparatus for measuring the blood gases. Although the gripping band 24 has been indicated as being made of rubber, it will be clear that, based on its purpose, the band 24 may be made from any resilient material having a high coefficient of friction.

Turning now to FIG. 2, there is illustrated the gas lock of the instant invention further including the cap previously referred to. FIG. 2 illustrates a cap 30 positioned in a container 14. The purpose of the cap 30 (which is shown in greater detail in FIG. 3 below) is to provide additional support for the hypodermic unit indicated in phantom lines at 32. Comparing FIGS. 1 and 2, it may be seen that in the embodiment illustrated in FIG. 1 (not including a cap), the hypodermic unit is not supported at any point above the upper portion 8 of the needle 4. Although this support is, for most purposes, sufficient, it will be seen that under some conditions it is possible for the needle 4 to be broken away from the syringe portion 2. The embodiment illustrated in FIG. 2 provides support for the hypodermic unit up to the junction of the needle 4 and the syringe 2, thereby providing additional support and minimizing the likelihood of the needle breaking away from the syringe.

FIG. 3 is a plan view, partly in cross section, taken along the line 3—3 of FIG. 2. As illustrated in FIG. 3, the cap 30 includes a gripping band 34 which may be made of the same material as is used for the gripping band 24. The gripping band 34, as may be seen in FIG. 3, serves to firmly grip and support both the uppermost portion of the needle 4, indicated at 36, and the lowermost portion of the syringe 2, indicated at 38. It may thus be seen that utilization of the embodiment of FIGS. 2 and 3, that is, the embodiment of the gas lock utilizing a cap, provides additional support for the hypodermic unit, thereby minimizing the likelihood of breakage.

Turning now to FIG. 4, there is shown a detailed view of the portion 8 of the needle 4. As illustrated in FIG. 4, the portion 8 is formed with a plurality of vertically extending ribs 40 which are provided for the purpose of increasing the rotational friction between the needle 4 and the gripping band 24, thereby facilitating the twisting and removal of the needle 4 from the syringe 2 preparatory to the testing of the blood within the syringe.

It may now be seen that there has been illustrated and described a gas lock suitable for use with a hypodermic unit which insures the integrity of the gases contained within the unit; which is relatively inexpensive; and which reduces the hazards to medical personnel handling the unit.

It will be understood that the foregoing description of the preferred embodiments of the present invention are for purposes of illustration only, and that the various structural and operational features as herein disclosed are susceptible to a number of modifications and changes, none of which entails any departure from the spirit and scope of the present invention as defined in the hereto appended claims.

What is claimed is:

1. A gas lock for a hollow needle having a puncturing end comprising:
   a hypodermic syringe comprising a syringe removably connected to said hollow needle;
   a container in contact with said syringe and adapted to receive the puncturing end of said needle, said container having an open upper end portion and a closed lower end portion; and
   a semi-solid substance filling at least the lower portion of said container and positioned to be penetrated by, and to envelop, the puncturing end of said needle, to prevent gas from escaping from, or entering into, the puncturing end of said needle, and the interior portion of said container above said semi-solid substance being at least partially filled with a porous solid material.

2. A gas lock according to claim 1 further comprising gripping means positioned in the upper portion of said container, said gripping means being adapted to grip the end of said needle opposite said puncturing end.

3. A gas lock for sealing blood gases in a collection vessel used to collect blood for blood gas analysis comprising:
   a hypodermic unit consisting of a syringe removably interconnected to a hollow needle having a puncturing end,
   a container having an open upper end and a sealed lower portion, said container being coaxially disposed around said needle,
   a semi-solid substance located within at least the lower portion of said container for penetrating and enveloping the puncturing end of said needle,
   means for gripping said needle located in the upper portion of said container above said semi-solid substance,
   said needle penetrating said semi-solid substance and said puncturing end being positioned in and enveloped by said semi-solid substance.

4. The gas lock arrangement of claim 3 wherein said container is removably positioned on said hypodermic unit, and said container includes a porous solid material in the upper portion thereof above said semi-solid substance.

5. The gas lock arrangement according to claim 4 wherein said semi-solid substance is a mixture of petroleum jelly and paraffin.

6. The gas lock arrangement of claim 5 wherein said porous solid material is rubber.

7. The gas lock arrangement according to claim 6 comprising a cap seated on the upper end of said container, said cap encircling said hypodermic unit in the region where said needle and said syringe communicate with one another.

8. The gas lock arrangement according to claim 7 wherein said cap included a rubber gripping band within the upper portion of said container, said gripping band contacting the uppermost portion of said needle and the lowermost portion of said syringe.

9. The gas lock arrangement of claim 7 wherein said means for gripping said needle comprises a resilient material having a high coefficient of friction.

10. The gas lock arrangement of claim 4 wherein said semi-solid substance is a caulking compound.

11. The gas lock arrangement of claim 4 wherein said porous solid material is styrofoam.

* * * * *